US00PP07804P

United States Patent [19]

Carrier et al.

[11] Patent Number: Plant 7,804

[45] Date of Patent: Feb. 25, 1992

[54] ALSTROEMERIA NAMED ELENA

[75] Inventors: Leonard E. Carrier, Encinitas, Calif.; Stephen Garton, West Jordan, Utah

[73] Assignee: Native Plants, Incorporated, Salt Lake City, Utah

[21] Appl. No.: 512,159

[22] Filed: Apr. 20, 1990

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Venable, Baetjer, Howard & Civiletti

[57] ABSTRACT

This plant is particularly characterized by its dwarf habit which makes the plant eminently suitable for cultivation as a potted plant. In addition, the plant bears several flowering stalks which carry large attractive flowers which are predominantly of a pale purple coloration. The attractive flowers and desirable growth habit of this new plant provides a novel addition to the range of Alstroemerias.

1 Drawing Sheet

BACKGROUND OF THE NEW PLANT

This new variety of Alstroemeria originated as a seedling resulting from crossing two plants growing among a collection of breeding stock maintained in a greenhouse in Encinitas, Calif. The seedling was selected for further propagation and testing because of the dwarf characteristic of the whole plant, and the attractive color of the many large flowers contained in several inflorescences as the plant bloomed in a pot. The select plant was propagated in Salt Lake City, Ut., by division of the rhizomatous rootstock and through tissue culture. The distinguishing characteristics of the new plant hold true in successive vegetative generations and appear to be firmly fixed. Propagation work is currently being carried out in Salt Lake City using tissue culture methods.

DESCRIPTION OF THE DRAWING

This new variety of Alstroemeria plant is illustrated by the accompanying photographic drawing in full color showing a blooming umbel of the plant with buds and flowers in different stages of flower development. The color renditions are believed to be as close to the specified color as is possible to obtain by conventional photographic procedures.

DESCRIPTION OF THE NEW PLANT

The following is a detailed description of the new Alstroemeria variety with color designations according to The R.H.S. Colour Chart of The Royal Horticultural Society of London, England. The observations were made on plants grown in a greenhouse in Utah County, Ut., during the summer.

THE PLANT

Origin: Seedling (73-BE-80A).

Parentage:

*Seed parent.*—Breeding stock plant No. BE.

*Pollen parent.*—Breeding stock plant No. 80A.

Classification: Alstroemeria hybrid.

Form: Compact, erect bush with a slightly spreading habit having several flower stalks bearing branches with simple umbel arrangement at the tops.

Height: About 35 to 45 cm.

Growth: Erect, vigorous and strong.

Rootstock: Rhizomatous, the rhizomes bear numerous buds which give rise to vegetative and reproductive shoots throughout the growth period. Rhizomes also produce roots, some of which become tuberous.

Foliage:

*Quantity.*—Medium, about 25 to 35 leaves per stem.

*Leaf size.*—About 11 cm.

*Leaf shape.*—Elliptical.

*Texture.*—Waxy.

*Color.*—Upper surface — Green, Lower surface — Grey-green.

THE BUD

Form: Pear-shaped. The six petals are perianth and there is no calyx.

Size: Medium.

*Diameter.*—9.0 mm.

*Length.*—1.8 cm.

Length of peduncle: 2.5 to 3.5 cm.

THE FLOWER

Blooming habit: Continuous and freely flowering throughout the season.

Flower size: Medium.

*Diameter.*—About 5.5 cm.

*Length.*—About 6.5 cm.

Shape: Generally funnel-like.

Borne: Singly.

Petalage:

*Number.*—Six.

*Arrangement.*—Two Concentric circles of three.

*Form.*—Outer petals — Obcordate, Inner petals — Elliptical.

*Texture.*—Smooth.

*Appearance.*—Satiny.

*Color.*—Outer petals — There is a small green protuberance 147B, central on the upper margin which is subtended by a pale green area 145D. There is a patch of red-purple, 64B, in the middle of the distal half. The remainder of the petal is pale purple 76D. The reverse surface is red-purple, 70B, with pale purple areas, 76D, on the upper lateral margins. Three green, longitudinal veins originate from the green protruberance and extend over the distal half of the petal through a distinct red-purple patch, 64B, on the distal half of the petal. Inner petals — Upper; The small pointed tip is light green. In the mid section of the pale purple petal, 76D, is a central pale yellow patch, 3B. There are longitudinal streaks of greyed-purple, 187A, covering the petal. These streaks are most prominent on the distal portion. The distal and medial portions of the reverse surface are pale purple, 76D. Distally there is a splash of red-purple 70B below which, there is a pale yellowish green spot, 144D. The basal part is red-purple, 68D. The streaks on the other surface are visible through the petal. Lower; There is a small, pointed, green tip on the upper margin. The petal is pale purple, 76D, with a longitudinal splash of red-purple in the mid section. Longitudinal, greyed-purple streaks, 187A, are visible on the distal half. The reverse surface is a pale purple, 76D, with two prominent longitudinal splashes central on the distal half. The streaks on the other surface are visible through the petal.

Persistence.—The flowers hang and dry.

Lasting quality.—On the plant, 14–18 days.

Main stem or stalk:

*Length.*—40 to 55 cm.

*Color.*—Green.

*Character.*—Upright, and strong.

REPRODUCTIVE ORGANS

Stamens:

*Number.*—Six.

*Arrangement.*—One opposite each petal.

*Anthers.*—Size: 7.0 mm. Color — Grey.

*Filaments.*—Length: About 4.7 cm. Color: Pink.

*Pollen.*—Color: Light grey-brown.

Pistils:

*Number.*—One.

*Style.*—Length: About 4.0 cm. Color: Pink.

*Stigma.*—Color: Pink.

Fruit:

*Shape.*—Capsular; Color — Light brown at maturity.

What is claimed:

1. A new and distinctive Alstroemeria hybrid, substantially as shown and described herein, characterized by a dwarf habit and large predominately pale purple colored flowers, which are borne in attractive inflorescences on relatively dwarf flower stalks.

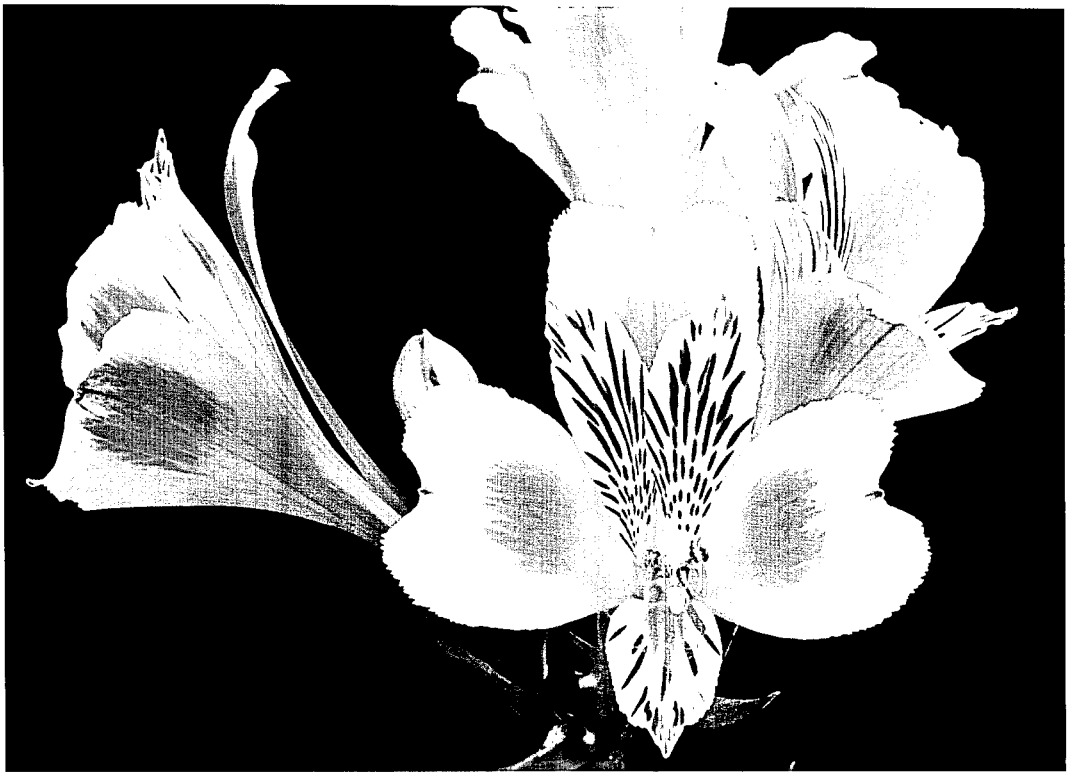

* * * * *